(12) United States Patent
Caleffi et al.

(10) Patent No.: US 8,747,342 B2
(45) Date of Patent: Jun. 10, 2014

(54) AIR SEPARATOR FOR EXTRACORPOREAL FLUID TREATMENT SETS

(75) Inventors: Luca Caleffi, Mirandola (IT); Francesco Ribolzi, Varese (IT); Ranko Sakota, Giugliano In Campania (IT)

(73) Assignee: Gambro Lundia AB, Lund (SE)

( * ) Notice: Subject to any disclaimer, the term of this patent is extended or adjusted under 35 U.S.C. 154(b) by 1069 days.

(21) Appl. No.: 12/447,641

(22) PCT Filed: Oct. 30, 2006

(86) PCT No.: PCT/IB2006/003038
§ 371 (c)(1),
(2), (4) Date: Apr. 26, 2010

(87) PCT Pub. No.: WO2008/053261
PCT Pub. Date: May 8, 2008

(65) Prior Publication Data
US 2010/0292627 A1      Nov. 18, 2010

(51) Int. Cl.
*A61M 37/00*      (2006.01)
(52) U.S. Cl.
USPC ........................................... 604/6.15
(58) Field of Classification Search
USPC .............. 604/4.01, 5.01, 6.09, 6.15, 317, 321
See application file for complete search history.

(56) References Cited

U.S. PATENT DOCUMENTS

| | | | |
|---|---|---|---|
| 3,878,095 A * | 4/1975 | Frasier et al. | 210/87 |
| 4,061,031 A * | 12/1977 | Grimsrud | 73/200 |
| 4,263,808 A | 4/1981 | Bellotti et al. | |
| 4,344,777 A | 8/1982 | Siposs | |
| 4,436,620 A * | 3/1984 | Bellotti et al. | 210/90 |
| 4,439,189 A * | 3/1984 | Sargeant et al. | 604/317 |
| 4,468,329 A * | 8/1984 | Shaldon et al. | 210/651 |
| 4,666,598 A | 5/1987 | Heath et al. | |
| 4,681,606 A | 7/1987 | Swan, Jr. et al. | |
| 4,702,829 A * | 10/1987 | Polaschegg et al. | 210/195.2 |
| 4,711,715 A * | 12/1987 | Polaschegg | 210/103 |
| 4,715,959 A * | 12/1987 | Allan et al. | 210/637 |
| 4,770,787 A * | 9/1988 | Heath et al. | 210/646 |
| 4,798,090 A | 1/1989 | Heath et al. | |
| 4,863,452 A | 9/1989 | Irmiter et al. | |
| 4,997,570 A * | 3/1991 | Polaschegg | 210/646 |
| 5,024,756 A * | 6/1991 | Sternby | 210/93 |
| 5,211,849 A * | 5/1993 | Kitaevich et al. | 604/5.04 |
| 5,247,434 A * | 9/1993 | Peterson et al. | 700/83 |
| 5,326,476 A * | 7/1994 | Grogan et al. | 210/646 |

(Continued)

FOREIGN PATENT DOCUMENTS

| | | |
|---|---|---|
| CN | 1 569 265 A | 1/2005 |
| EP | 0 058 325 B1 | 3/1985 |
| EP | 0 800 838 A2 | 10/1997 |

*Primary Examiner* — Susan Su
*Assistant Examiner* — Guy K Townsend
(74) *Attorney, Agent, or Firm* — Pearne & Gordon LLP (57) ABSTRACT

An air separator (1) comprises a first chamber (2) where blood or other fluid can be received, an inlet and an outlet port associated to the bottom wall (4) and in fluid communication with the first chamber. A first channel (14) extending along the lateral wall of the separator and has a first and a second portion (16 and 18). The channel second portion (18) terminally forms an orifice (15) facing the chamber and extending in an area closer to a top wall (5) of the chamber (2) than to the bottom wall of the same chamber. The orifice faces the top of the separator and has a flow passage cross section greater than that of a first portion (16) of the channel.

33 Claims, 12 Drawing Sheets

(56) References Cited

U.S. PATENT DOCUMENTS

| | | | | |
|---|---|---|---|---|
| 5,344,568 A | * | 9/1994 | Kitaevich et al. | 210/645 |
| 5,397,299 A | * | 3/1995 | Karwoski et al. | 604/6.1 |
| 5,441,636 A | * | 8/1995 | Chevallet et al. | 210/232 |
| 5,487,827 A | * | 1/1996 | Peterson et al. | 210/87 |
| 5,591,251 A | * | 1/1997 | Brugger | 95/242 |
| 5,591,344 A | | 1/1997 | Kenley et al. | |
| 5,605,540 A | | 2/1997 | Utterberg | |
| 5,630,935 A | | 5/1997 | Treu | |
| 5,645,734 A | | 7/1997 | Kenley et al. | |
| 5,651,893 A | | 7/1997 | Kenley et al. | |
| 5,658,456 A | | 8/1997 | Kenley et al. | |
| 5,662,806 A | * | 9/1997 | Keshaviah et al. | 210/739 |
| 5,670,050 A | | 9/1997 | Brose et al. | |
| 5,674,390 A | | 10/1997 | Matthews et al. | |
| 5,674,397 A | | 10/1997 | Pawlak et al. | |
| 5,674,404 A | | 10/1997 | Kenley et al. | |
| 5,690,821 A | | 11/1997 | Kenley et al. | |
| 5,690,831 A | * | 11/1997 | Kenley et al. | 210/646 |
| 5,702,606 A | * | 12/1997 | Peter et al. | 210/646 |
| 5,705,066 A | | 1/1998 | Treu et al. | |
| 5,707,086 A | | 1/1998 | Treu et al. | |
| 5,714,060 A | | 2/1998 | Kenley et al. | |
| 5,725,776 A | * | 3/1998 | Kenley et al. | 210/646 |
| 5,788,099 A | | 8/1998 | Treu et al. | |
| 5,863,421 A | | 1/1999 | Peter, Jr. et al. | |
| 5,932,110 A | | 8/1999 | Shah et al. | |
| 5,941,842 A | * | 8/1999 | Steele et al. | 604/4.01 |
| 6,083,187 A | | 7/2000 | Nakayama et al. | 604/6.01 |
| 6,200,485 B1 | * | 3/2001 | Kitaevich et al. | 210/739 |
| 6,284,131 B1 | | 9/2001 | Hogard et al. | 210/143 |
| 6,287,516 B1 | | 9/2001 | Matson et al. | 422/44 |
| 6,303,036 B1 | * | 10/2001 | Collins et al. | 210/646 |
| 6,406,631 B1 | * | 6/2002 | Collins et al. | 210/646 |
| 6,423,231 B1 | * | 7/2002 | Collins et al. | 210/646 |
| 6,468,427 B1 | * | 10/2002 | Frey | 210/497.01 |
| 6,582,385 B2 | * | 6/2003 | Burbank et al. | 604/5.04 |
| 6,736,972 B1 | * | 5/2004 | Matson | 210/650 |
| 6,780,322 B1 | * | 8/2004 | Bissler et al. | 210/637 |
| 6,821,431 B2 | * | 11/2004 | Collins et al. | 210/646 |
| 6,913,588 B2 | * | 7/2005 | Weitzel et al. | 604/6.09 |
| 6,949,214 B2 | * | 9/2005 | Frey | 264/328.1 |
| 7,067,060 B2 | * | 6/2006 | Collins et al. | 210/646 |
| 7,115,107 B2 | * | 10/2006 | Delnevo et al. | 604/6.15 |
| 7,264,607 B2 | * | 9/2007 | Caleffi | 604/6.16 |
| 7,285,105 B2 | * | 10/2007 | Kim et al. | 604/5.04 |
| 7,291,122 B2 | * | 11/2007 | Matson | 604/6.09 |
| 2001/0041892 A1 | * | 11/2001 | Burbank et al. | 606/46 |
| 2001/0045395 A1 | * | 11/2001 | Kitaevich et al. | 210/739 |
| 2001/0051106 A1 | * | 12/2001 | Matson et al. | 422/44 |
| 2003/0130607 A1 | * | 7/2003 | Delnevo et al. | 604/4.01 |
| 2003/0217972 A1 | * | 11/2003 | Connell et al. | 210/646 |
| 2003/0222022 A1 | * | 12/2003 | Connell et al. | 210/636 |
| 2004/0024342 A1 | * | 2/2004 | Weitzel et al. | 604/5.01 |
| 2004/0050789 A1 | * | 3/2004 | Ash | 210/646 |
| 2004/0069709 A1 | * | 4/2004 | Brugger et al. | 210/646 |
| 2004/0084372 A1 | * | 5/2004 | Connell et al. | 210/646 |
| 2004/0186416 A1 | * | 9/2004 | Caleffi | 604/6.16 |
| 2004/0219059 A1 | * | 11/2004 | Barringer et al. | 422/44 |
| 2005/0020958 A1 | * | 1/2005 | Paolini et al. | 604/4.01 |
| 2005/0029193 A1 | * | 2/2005 | Matson | 210/645 |
| 2005/0040110 A1 | * | 2/2005 | Felding | 210/646 |
| 2005/0045548 A1 | * | 3/2005 | Brugger et al. | 210/252 |
| 2005/0054968 A1 | | 3/2005 | Giannella | |
| 2005/0065459 A1 | * | 3/2005 | Zhang et al. | 604/4.01 |
| 2005/0082210 A1 | * | 4/2005 | Favre | 210/109 |
| 2005/0126961 A1 | * | 6/2005 | Bissler et al. | 210/87 |
| 2005/0131331 A1 | * | 6/2005 | Kelly et al. | 604/4.01 |
| 2005/0131332 A1 | * | 6/2005 | Kelly et al. | 604/4.01 |
| 2005/0230292 A1 | * | 10/2005 | Beden et al. | 210/85 |
| 2006/0084906 A1 | * | 4/2006 | Burbank et al. | 604/6.16 |
| 2010/0268145 A1 | * | 10/2010 | Caleffi et al. | 604/5.04 |

\* cited by examiner

Prior art

Prior art

AIR SEPARATOR FOR EXTRACORPOREAL FLUID TREATMENT SETS

FIELD OF THE INVENTION

The invention relates to an air separator for extracorporeal fluid treatment set. The air separator of the invention can for instance be used in extracorporeal blood treatment procedures, or in procedures involving extracorporeal displacement of blood or of blood components or of medical fluids.

BACKGROUND OF THE INVENTION

By way of non-limiting example and in order to provide a background to the present invention reference is made to the field of extracorporeal blood treatment.

As it is well known in the art, blood treatment apparatus, such as hemodialysis machines, are used to continuously remove impurities from a patient's blood. The blood is typically pumped through tubes and moved through arterial and/or venous bubble traps (air separators) associated to disposable tubing sets connecting the patient to a dialyzer or other treatment unit mounted on the hemodialysis machine.

U.S. Pat. No. 4,263,808 discloses a one-piece hydraulic circuit that includes arterial and venous bubble trap chambers in which blood enters at entrances above the bottoms of the chambers and leaves near the bottoms of the chambers. Pressure in the chambers can be determined by transducers placed against impermeable latex membranes covering holes communicating with upper portions of the chambers.

U.S. Pat. No. 4,666,598 discloses a fluid flow chamber cassette that can be mounted with either its front wall or rear wall against a supporting machine, such as a hemodialysis machine, and has a flexible tube that extends from a sidewall and forms a loop that is symmetrical about a loop axis that is transverse to the side wall so that the loop will be acted upon by a pump roller on the machine both when the front wall is against the machine and when the rear wall is against the machine. The orientation of the cassette and the direction of fluid flow through the cassette can thus be changed by simply changing whether the front or the rear wall is mounted against the machine. The cassette comprises an arterial chamber and a venous chamber. The arterial chamber inlet enters the arterial chamber at a position higher than the arterial chamber outlet, and the venous chamber inlet enter the venous chamber at a position higher than the venous chamber outlet. When priming by causing reverse flow, the liquid rises in the venous and arterial chambers to the levels of the entrances of the inlets, and the amount of air in the chambers remains fixed, even after flow is reversed during normal operation with blood. Each of the arterial and venous chambers has a corresponding impermeable flexible diaphragm over a hole in a rigid wall of the chamber for the purpose of sensing pressure.

So-called "bottom entry" chambers whereby the blood inlet port is at the bottom of the chamber and blood enters into the blood space at the bottom or sidewall of the chamber are known from U.S. Pat. No. 4,681,606, U.S. Pat. No. 4,666,598 and European Patent No. 0058325.

Finally, U.S. Pat. No. 5,605,540 discloses a one-piece, plastic, blow molded arterial or arterial-venous blood chamber with bottom entry having equal height inlet and outlet wherein both the inlet and outlet have a progressively increasing cross section when moving from the bottom to the top of the chamber.

Figure 7A:
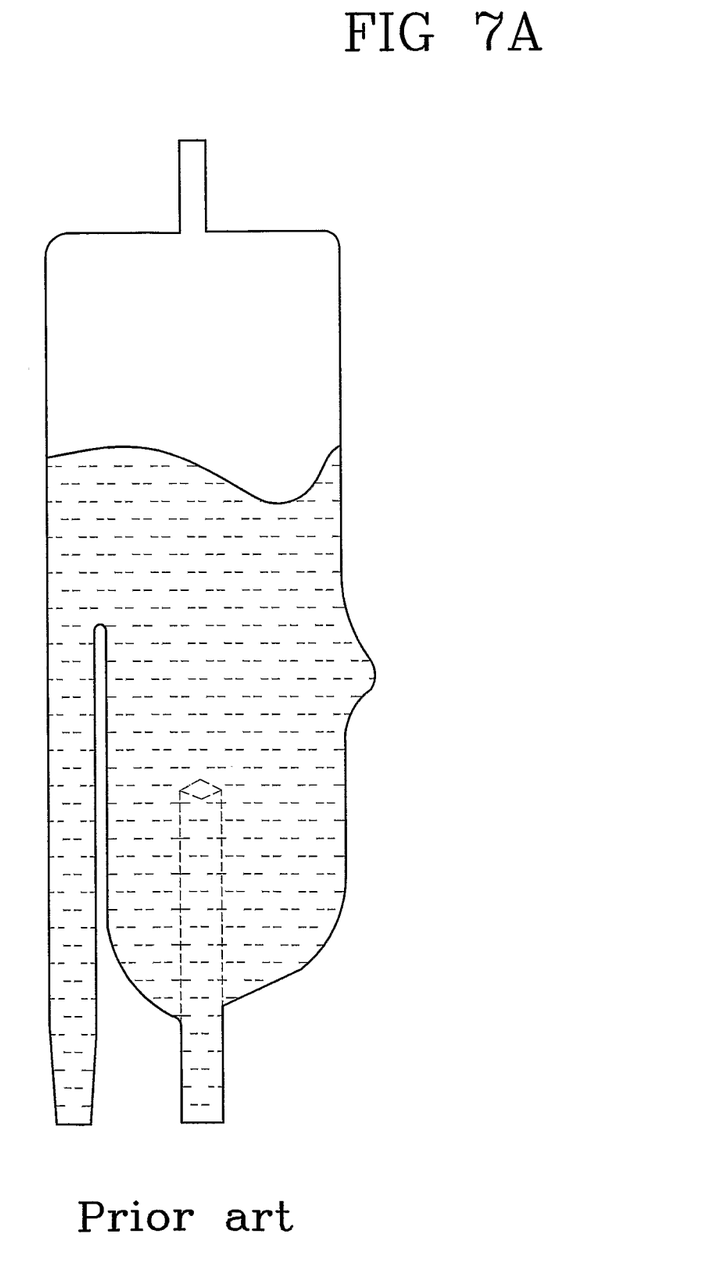
FIGS. 7A and 7B are schematic elevation views showing blood in a blood chamber of known design and in an air separator according to the invention respectively.
Figure 8A:
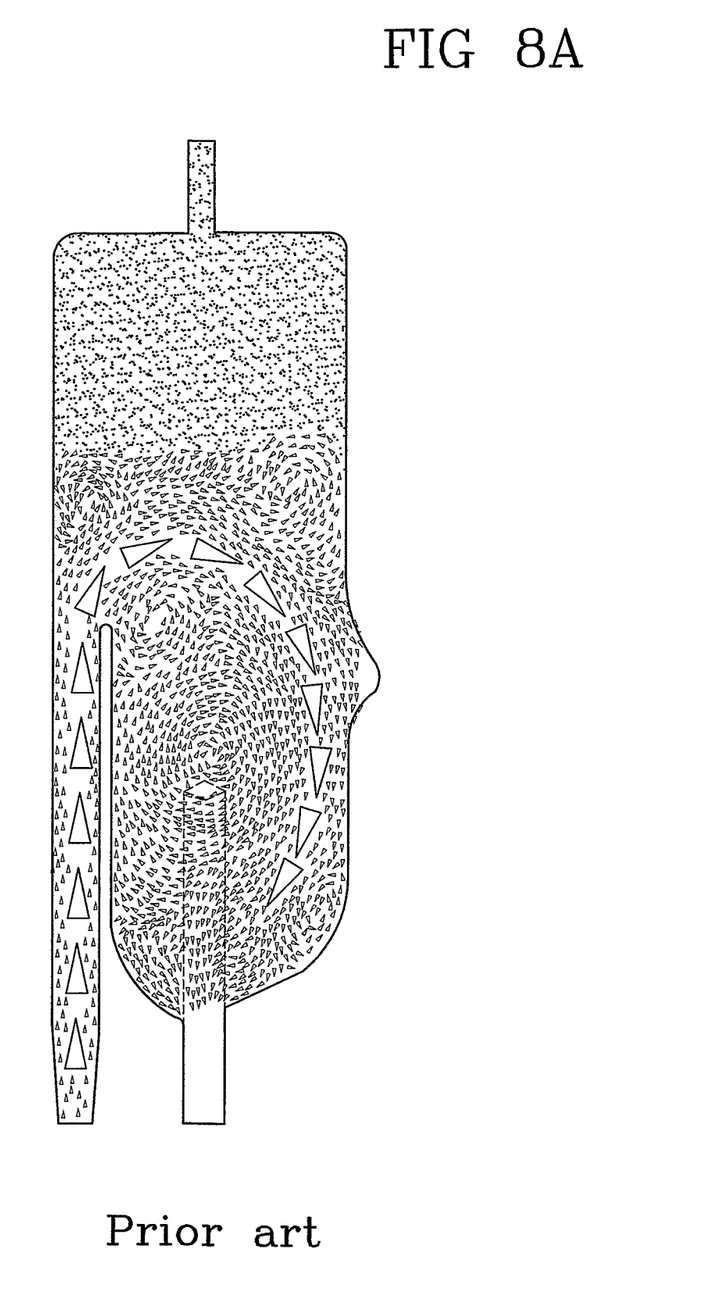
FIGS. 8A and 8B are schematic elevation views showing the flow speed pattern of blood in a blood chamber of known design and in an air separator according to the invention respectively.

Furthermore the applicant has in the past put on the market air separators as schematically shown in appended FIGS. 7A and 8A.

SUMMARY OF THE INVENTION

The applicant has found that the structure of the blood or medical fluid chambers could be further improved in order to:
  enhance air separation, and avoid that air bubbles undesirably reach the chamber outlet,
  minimize foam formation in correspondence of the blood inlet, which could lead to problems in efficient air separation, and
  reduce stagnation areas which could contribute to formation of clots.

The above aims are reached by an air separator according to the appended claims.

According an aspect of the present invention the orifice bringing blood or other fluid into the chamber of the air separator is relatively distant from the outlet port.

According to a further feature of the invention the orifice is oriented so as to direct the liquid towards the top of the blood chamber.

These provision leave time to flow deceleration allowing the bubbles to separate from blood before this latter reaches the outlet port.

A further aspect of the invention provides for an inlet (first) channel where flow speed is significantly reduced and flow stability increased using two or more consecutive portions of progressively increasing cross section. This results in a substantial reduction of foam formation and contributes to the separation of any air bubbles present in the incoming blood.

In accordance with another aspect of the invention the air separator presents a filter inside the chamber and the orifice is placed far enough from the area of interest of the filter, as it is desirable that bubbles are separated before reaching any zone where they could be trapped and then uncontrollably released to the patient. Moreover if the filter is positioned and extends in correspondence of an area sufficiently far from the inlet channel orifice, stagnation areas in correspondence of the filter surface are less probable.

Further characteristics and advantages will better emerge from the following description in relation to some preferred but non-exclusive embodiments of an air separator according to the invention.

SHORT DESCRIPTION OF THE DRAWINGS

The description will be made with reference to the figures of the accompanying drawings, provided by way of non-limiting example, in which.

DETAILED DESCRIPTION

Referring to the enclosed drawings, several non-limiting embodiment of an air separator 1 according to the invention are shown. By way of non-limiting example the detailed description will make reference to a use of the air separator for separating air bubbles from blood, as it is the case when the separator 1 is used in extracorporeal blood treatment sets. The air separator comprises a first and a second chamber 2 and 3 (see FIG. 6) positioned in side by side relationship with respect to each other. Of course, depending upon the circumstances, the air separator could comprise only the first chamber. The first chamber presents a respective bottom wall 4, a respective top wall 5, and a respective lateral wall 6 extending between the top and bottom walls 4 and 5. Similarly the second chamber has a respective bottom wall 7, a respective top wall 8, and a respective lateral wall 9 extending between the top and bottom walls 7 and 8. The lateral wall of the embodiments shown in the attached drawings is formed by flat portions: it is however to be understood that the lateral wall could be curved. Also the shape of the top and bottom walls is not limited to the specific shape shown in the attached drawings.

The bottom wall of each chamber is provided with respective inlet and outlet ports for the fluid coming in the chamber and going out of the chamber. For sake of clarity the inlet and outlet ports 10 and 11 of the first chamber 2 are herein referred to as first inlet port 10 and first outlet port 11, while the inlet and outlet ports of the second chamber are herein referred to as second inlet port 12 and second outlet port 13.

Figure 1:
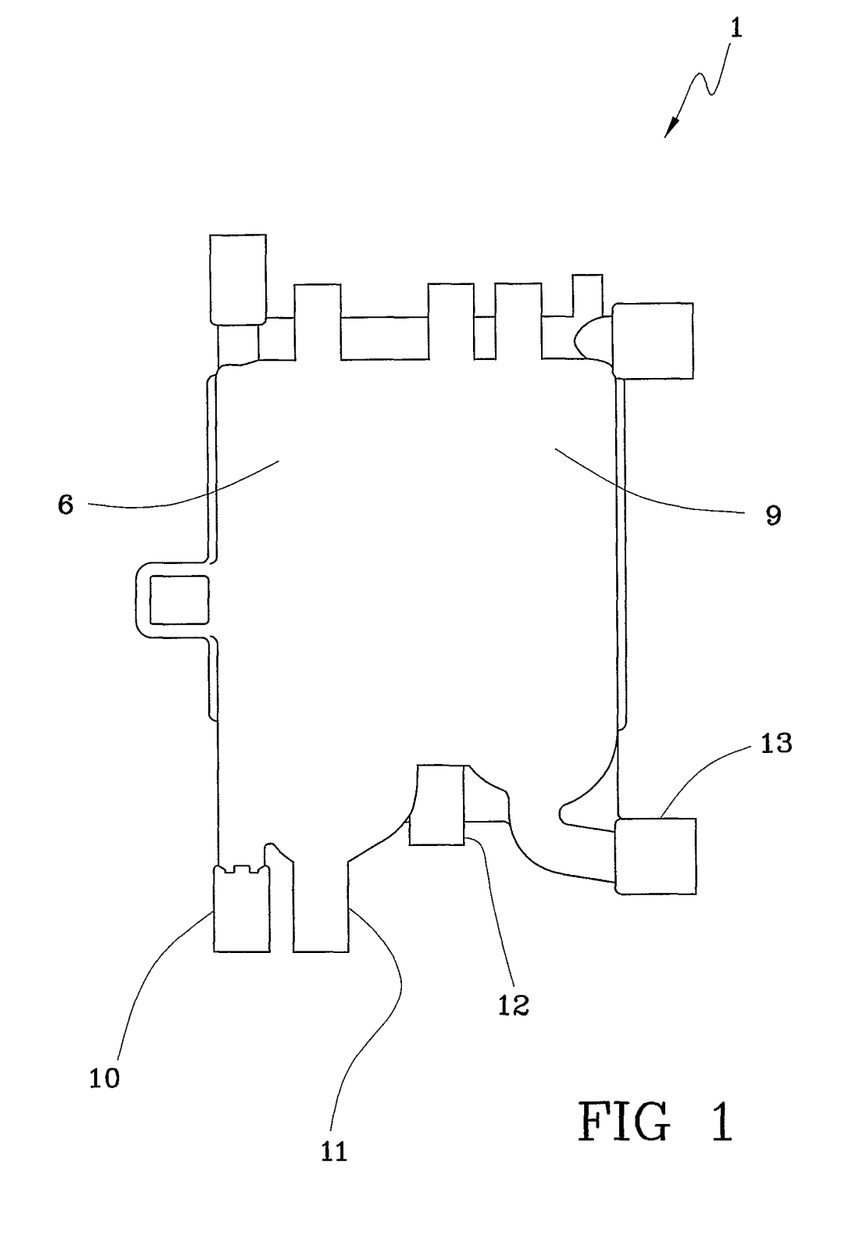
FIG. 1 is a front elevation of an air separator according to the invention.
Figure 2:
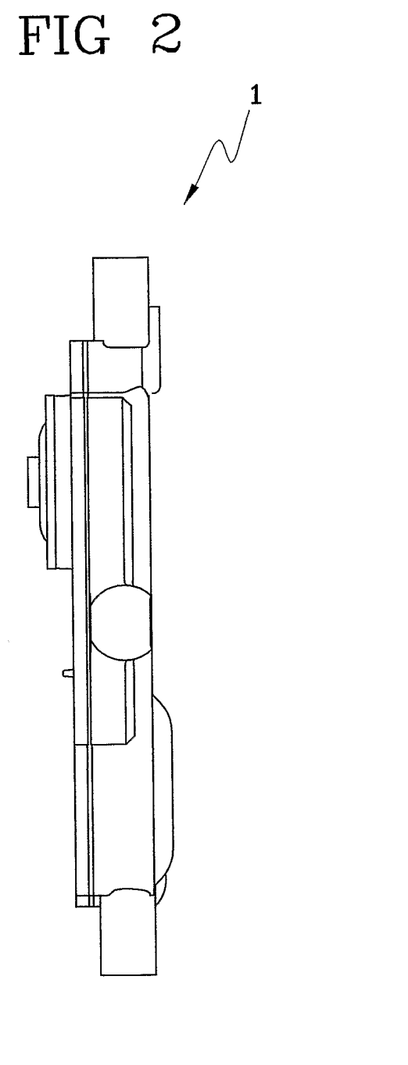
FIGS. 2 and 3 are side views of the separator of FIG. 1.
Figure 3:
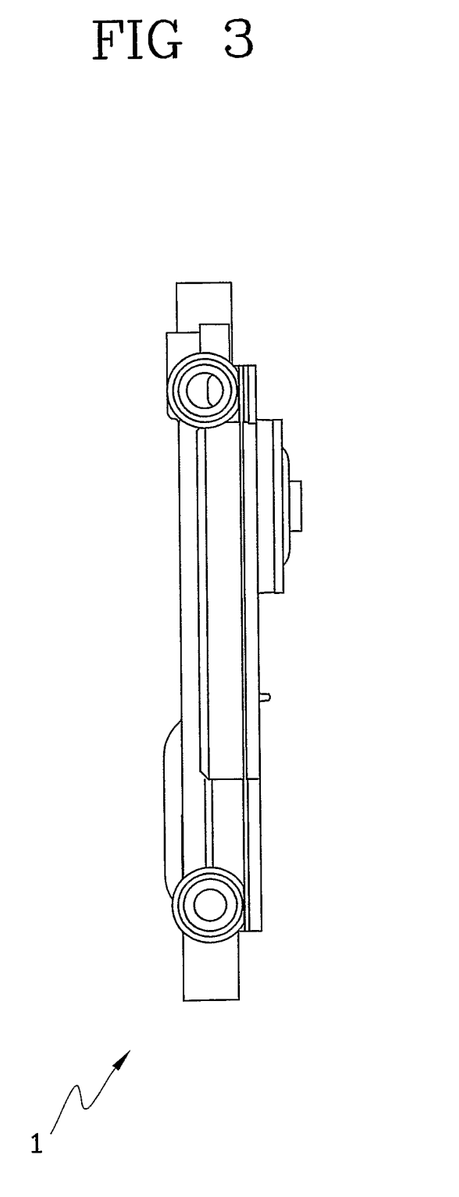

In all embodiments shown in the attached drawings, the air separator comprises a first channel 14 extending parallel to at least a portion 6a of the lateral wall 6 of the first chamber 2 and having a first end 14a, connected to the first inlet port 10, and a second end 14b, terminating into the first chamber in a position closer to said top wall 5 that to said bottom wall 4; the portion 6a is an inferior side part of the lateral wall. The second end 14b of the first channel 14 terminally delimits an orifice 15 which opens into the chamber and faces said top wall. Referring to a working condition, the plane of FIG. 1 represents a vertical plane and therefore the first channel develops vertically and the terminal orifice is substantially horizontal and faces the top of the air separator.

In all embodiments, the first channel has a first portion 16, directly connected to the first inlet port 10, and a second consecutive portion 18, defining a flow passage cross section greater then that of the first portion. Notice that 3 or more consecutive portions could be envisaged: in such a case too the cross section of the portions would increase moving away from the inlet port 10.

With the definition 'flow passage cross section' it is herein meant the net area available for fluid flow passage in correspondence of a certain section of a fluid channel or fluid chamber.

Fluid flowing into the first inlet port moves through the first relatively narrow portion and then through the second relatively large portion so that fluid speed is proportionally reduced when passing from the first to the second portion before entering the chamber 2.

Figure 10:
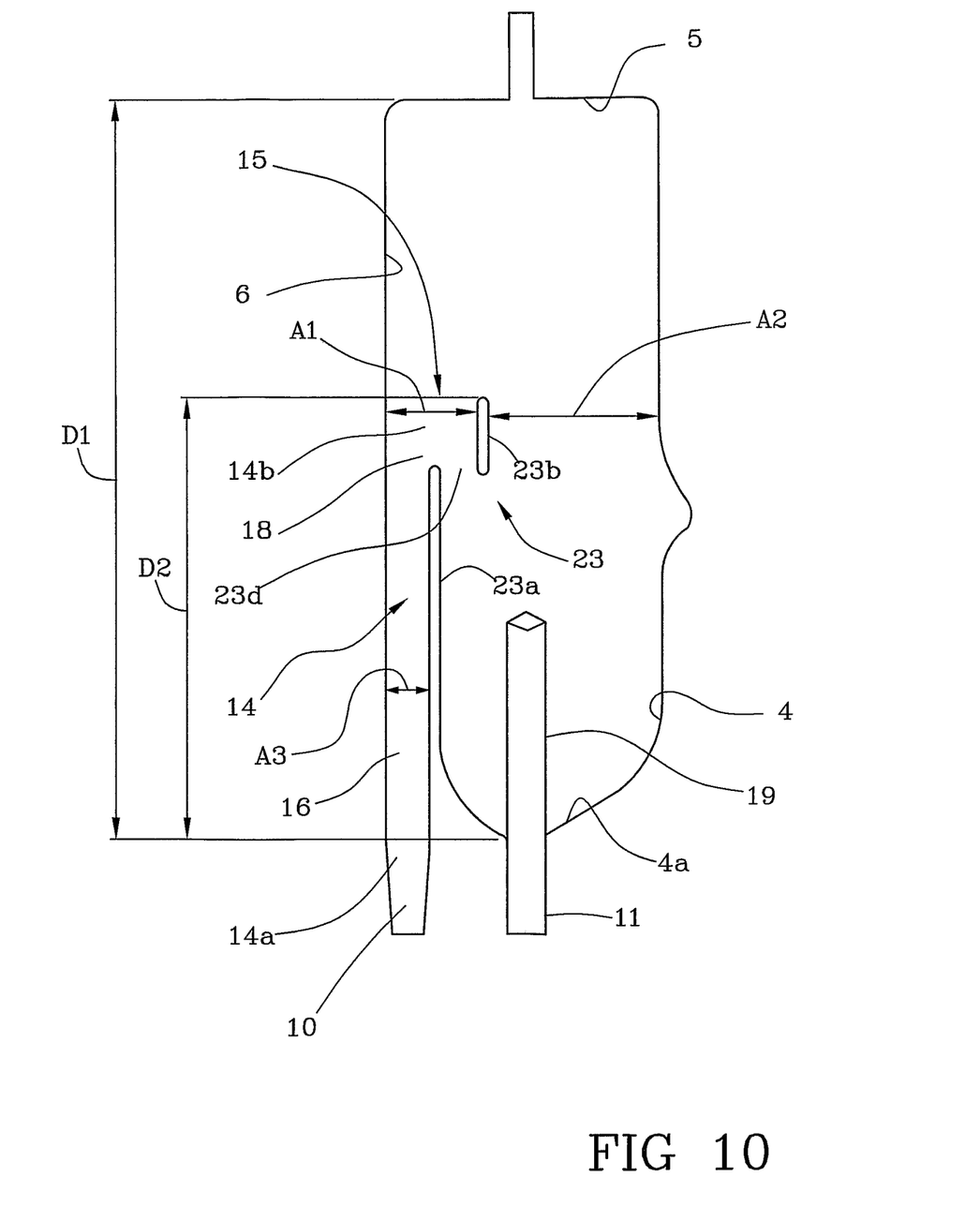

In the embodiment of FIGS. 1-6 and in the embodiment of FIG. 10 the first flow passage cross section and the second flow passage cross section are constant so as to define two tubular portions where the net area for the passage of fluid is constant and therefore flow speed can stabilize. FIG. 10 alternative embodiment has one chamber only: i.e. the first chamber. Notice however that the first chamber of FIG. 10 could be associated to a second chamber in a way similar to the embodiment of FIGS. 1-6.

Figure 6:
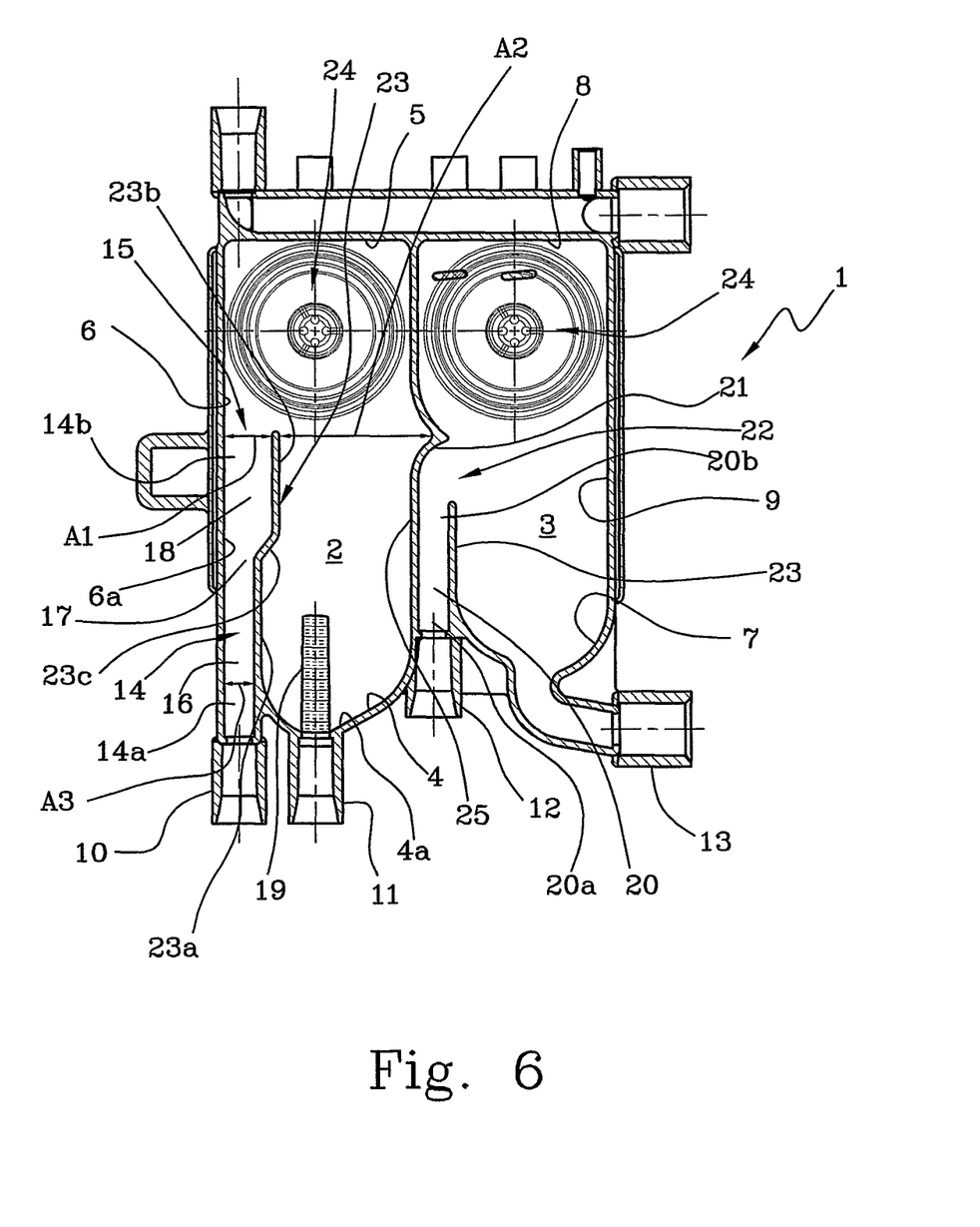
FIG. 6 is a section of the separator of FIG. 1.
Figure 9:
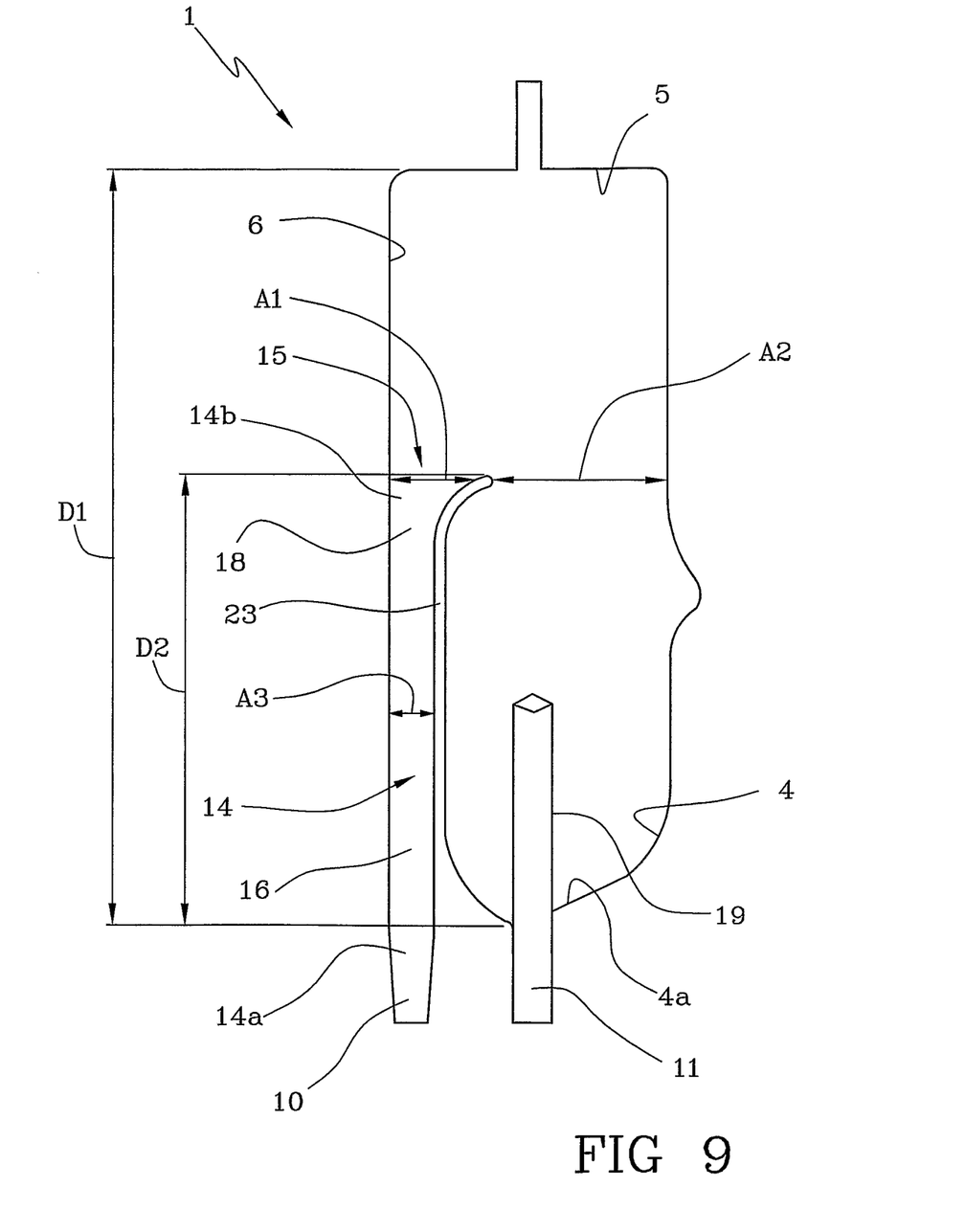
FIGS. 9 and 10 are schematic elevation views showing a separator according to possible alternative embodiments of the invention.

For a better understanding of the geometry of the air separators according to the invention and referring to non-limiting examples of FIGS. 6, 9 and 10, the following definitions are given:

D1 represents the measure of the distance between the top wall 5 inner surface and the bottom wall 4 inner surface (in some cases the top and/or the bottom wall could not be flat and parallel: in such cases D1 is the distance between the lowermost region of the bottom wall and the uppermost region of the top), D2 represents the measure of the distance between the horizontal plane where the orifice 15 of the first channel extends and the bottom wall (in some cases the bottom wall could not be flat and parallel to the horizontal: in such cases D1 is the distance between the horizontal plane containing the orifice and the lowermost region of the bottom), A1 represents the measure of the flow passage cross section area of the first channel 14 in correspondence of said orifice (referring to the enclosed examples A1 is measured taking a horizontal section in correspondence of the orifice), A2 represents the measure of the flow passage cross section area of the first chamber in correspondence of said orifice (referring to the enclosed examples A2 is measured taking a horizontal section of the first chamber at the same vertical position of the orifice), A3 represents the measure of the flow passage cross section area of the first channel in correspondence of the first portion 16 (referring to the enclosed examples A3 is measured taking a horizontal section in correspondence first portion).

In the embodiment of FIGS. 1-6, the first channel comprises a connection portion 17 consecutively connecting the second portion to the first portion and having a progressively increasing flow passage cross section. In practice the connection portion can be obtained by a wall portion inclined with respect to the direction of longitudinal development of each portion 16 and 18. In FIG. 10 embodiment, the two consecutive portions 16 and 18 are placed one downstream the other and an aperture in correspondence of the area of connection of the two portions. This aperture, together with the above mentioned orifice 15, serves to put the channel 14 into communication with the chamber and gives a preferential path for fluid coming from the inlet port 10 and not having enough kinetic energy to reach the orifice 15. In the embodiments of FIGS. 1-6 and 10, A1 is between 1.5 and 2.5 times A3.

FIG. 9 shows an alternative embodiment where the air separator 1 has one chamber only: i.e. the first chamber. Notice however that the first chamber of the embodiment shown in FIG. 9 could be associated to a second chamber in a way similar to the embodiment of FIGS. 1-6. In the embodiment of FIG. 9, the channel 14 presents a second portion 18 where the flow passage cross section increases in a progressive and continuous manner moving towards said second end (i.e. with reference to the attached figures the net area for the fluid passage increases moving closer to the top wall). According to a possible variant of the embodiment of FIG. 9, the channel 14 can present a continuously and progressively increasing flow passage cross section from said first to said second end.

Also in the embodiments of FIG. 9, A1 is between 1.5 and 2.5 times the measure of A3.

Returning to a description of features common to all embodiments, the first channel 14 has a longitudinal extension parallel to the lateral wall of the first chamber such that the orifice results to be positioned in a certain position relative to said top and said bottom walls. Using the above definitions D2/D1 is greater than 0.5 and for instance comprised between 0.55 and 0.7.

Moreover, the ratio A1/A2 is greater than 0.25, meaning that the fluid does not abruptly pass from a narrow channel into a large chamber but rather the flow passage cross section area of the first channel in correspondence of the orifice is at least ¼ (in the shown embodiments around ⅓) the flow passage cross section area of the first chamber in correspondence of the orifice (i.e. the area of the fluid passage in the first chamber measured at the same height of the orifice as shown in FIG. 9, see references A1 and A2). The ratio A1/A2 as above defined is has also an upper limit in that it is less then 1.00 and preferably less than 0.75, meaning that the orifice area is preferably smaller than the area of the first chamber in correspondence of the same section of the air separator.

The air separator can also comprise a filter 19 engaged to the bottom wall in correspondence of the outlet port 11 and axially extending into the chamber according to a direction substantially parallel to the first portion of the channel. The filter can have a substantially cylindrical or frusto-conical or conical overall shape and meshes designed depending upon the needs.

The filter extends axially into the chamber from the bottom wall 4 lowermost region 4a and presents an overall axial extension into the first chamber (which is identified as D3 in the attached drawings) sensibly less than D2. According to the embodiment of FIG. 1, the filter presents an overall axial extension D3 substantially not greater than 0.70 of D3. In the embodiments shown, the axial length of the filter is less then that of the first portion 16 of the first channel 14 so that the filter 19 remains sufficiently distant from the first channel orifice 15.

The air separator can also comprise a second channel 20 (as for instance in the embodiment of FIGS. 1-6) extending parallel to the lateral wall of the second chamber 3 and having a first end 20a, connected to the second inlet port 12, and a second end 20b terminating into the second chamber; the second channel has constant cross section and presents a deflector 21 in correspondence of its second end defining an orifice 22 facing the lateral wall 9 of the second chamber. In practice flow coming from the second inlet moves through the second channel and (with reference to use conditions) turns substantially by 90°, thereby horizontally entering into the second chamber.

The orifice 22 faces the lateral wall 9 and extends across an area which is below the horizontal plane where the orifice 15 of the first channel lies (again with reference to a use condition of the separator).

Under a structural perspective, the overall air separator of the shown embodiments has a flattened configuration where said first channel and said first chamber have a substantially square shaped transverse section. The separator can be made in rigid and transparent plastic material. By way of non limiting example one of the following plastic materials could be used: PETG, PVC; however, any other suitable material could be of course equivalently used without departing from the scope of the invention which is directed to the geometry of the separator rather then to the specific materials used for the manufacture.

For instance the following materials could represent alternative choices for the separator manufacturing: Copolyester (e.g. Eastar copolyester PETG from Eastman Chemical Company), Acrylic-based multipolymer compounds (e.g. Cyrolite® trademark of Cyro Industries), Styrene-Butadiene block copolymer (S/B/S) (e.g. Styrolux® from BASF), MABS (e.g. Terlux® from BASF), Styrene-Methyl-Methacrylate-Butadiene polymers (e.g. Zylar® or NAS® from Nova Chemicals).

The entire air separator is made can be in one single piece, for instance by injection molding. In particular, the first channel 14 and the first chamber walls 4,5,6 are in one single plastic piece where the channel 14 presents a lateral wall having a longitudinal portion in common with a portion of the first chamber lateral wall. Similarly, when present, the second blood chamber can be in one piece with the first blood chamber and integrally bears the second channel 20.

In the embodiment of FIG. 6, each one of the first and second blood chambers presents a lateral wall formed by a front wall, a rear wall spaced from the front wall, side walls extending between said front and rear walls. The first and second chamber are joined in correspondence of one common side wall 25 which extends in correspondence of a central zone of the air separator; the front and rear walls of each chamber are coplanar and cooperate to define the front and rear walls of the entire air separator. An intermediate wall 23 extends between the front and rear walls of each blood chamber and laterally delimits the respective channel in cooperation with one of said side walls. In FIG. 6, the intermediate wall 23 associated with the first blood chamber presents a first wall portion 23a parallel to one of the side walls, a second wall portion 23b parallel to the same side wall and a deflecting portion 23c connecting said first and second portion thereby forming said first and second portions 16 and 18 as well as portion 17. In FIG. 9 the wall 23 presents a terminal curved portion defining the second portion 18 of first channel 14. In FIG. 10 the intermediate wall 23 is defined by two (or more) wall portions 23a and 23b separated by an aperture 23d.

The lateral wall of the first chamber can be designed to include pressure transducer means 24. In such a case the first channel ends immediately below said pressure transducer means. Also the second chamber can have respective pressure transducer means 24.

The pressure transducer means can include a hole on the air separator wall and a respective diaphragm tightly occluding the hole. The diaphragm is subject to deformation under the action of a pressure difference between the inside and the outside of each respective chamber and transmits a corresponding pressure signal to a tube connected to a pressure sensor inside the dialysis machine (or other treatment machine). U.S. Pat. No. 4,666,598 discloses in detail a possible embodiment for the pressure transducer means of the type just described. The pressure transducer means could also be different from the above described solution: for instance the diaphragm could be integrally in the obtained in the side wall by a thickness reduction in the wall which defines a movable part integral with the rest of the wall. According to a further alternative pressure could be detected via respective lines bringing the air to corresponding transducers remote from the air separator. Still another alternative provides for pressure sensors directly integrated on the separator wall and directly providing an electric signal function of the pressure inside the separator (piezoelectric sensors could be used). However, the way pressure in the blood chambers is detected is however not relevant for the present invention and any alternative means could equivalently be adopted.

Figure 11:
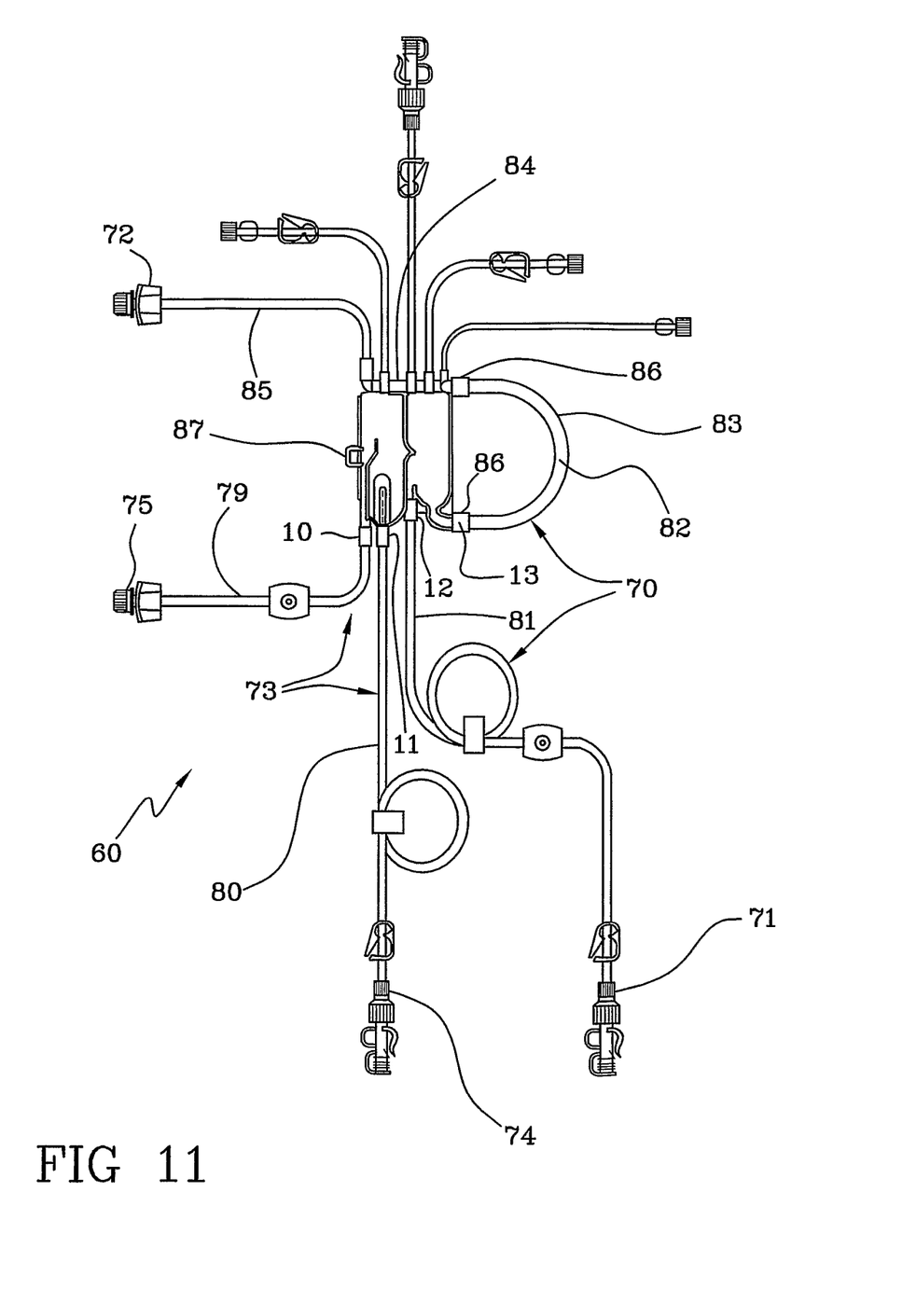
FIG. 11 is an elevation view showing a blood circuit where the air separator of FIG. 1 could be used.

FIG. 11 discloses an extracorporeal blood circuit 60 wherein air separator 1 of the type of FIGS. 1-6 is used.

The blood circuit 60 comprises an arterial line 70 which has at least one end 71 designed to be connected to a patient and another end 72 designed to be connected with a blood treatment unit, a venous line 73 which has at least one end 74 designed to be connected to a patient and another end 75 designed to be connected with a blood treatment unit.

The air separator of present invention is associated to the venous and arterial lines as here below described in details.

Figure 4:
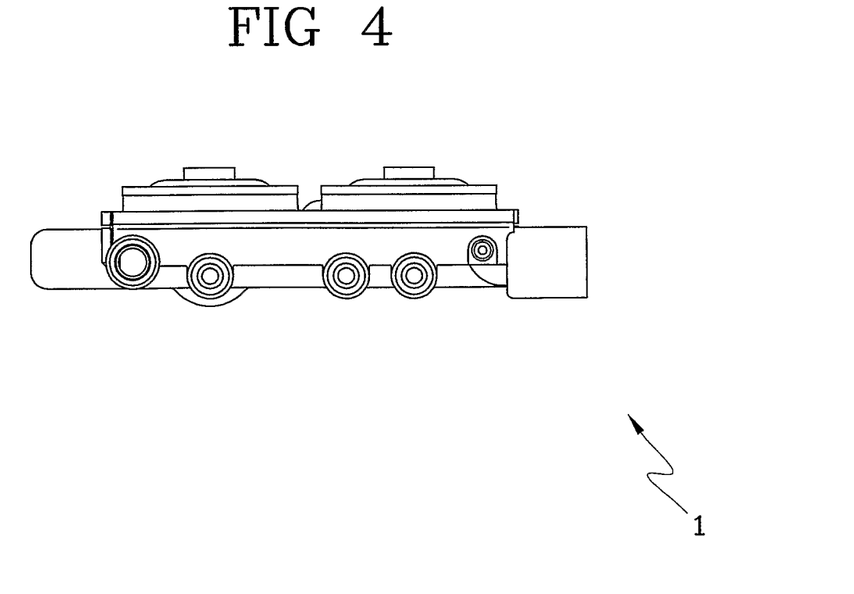
FIGS. 4 and 5 are top and bottom views of the separator of FIG. 1.
Figure 5:
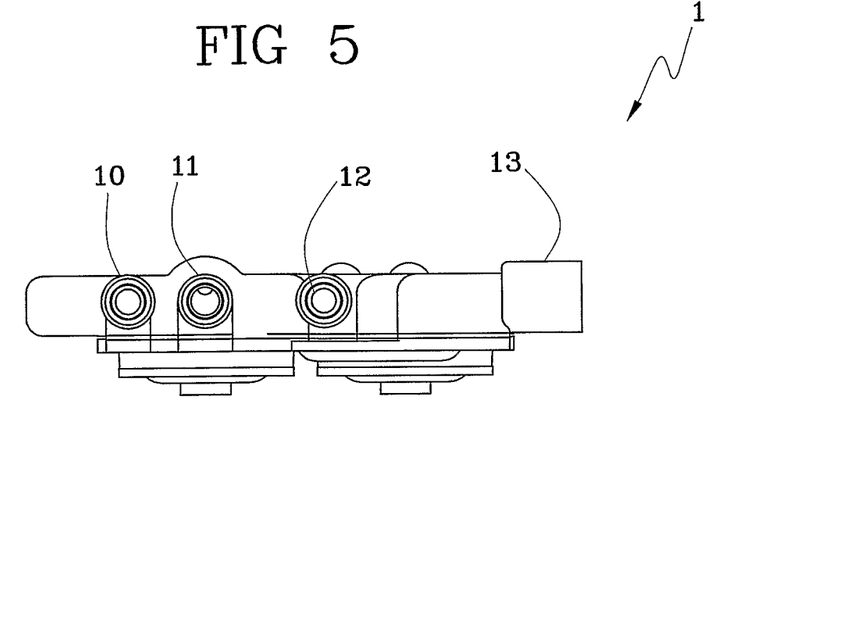

The venous line 73 includes a first flexible tube 79 having one end engaged to the inlet port 10 of the first blood chamber 2 and the opposite end 75 where a connector can be present. The venous line also includes a second flexible tube 80 having one end engaged to the outlet port 11 of the first blood chamber and the other end, which has already been identified with reference numeral 74, being for connection with a patient (via an access device not shown in the attached drawings). The arterial line 70 includes a third flexible tube 81 engaged to the inlet port 12 of the second blood chamber and terminating in correspondence of said end 71. The arterial line also includes a fourth flexible tube 82 engaged to the outlet port 13 of the second blood chamber and to one wall of said second blood chamber for forming a loop 83 which is symmetric about a loop axis transverse to the lateral wall of the second chamber. In the embodiment of FIG. 4 the tube 82 connects the outlet port 13 with a rigid channel 84 extending above the chambers 2 and 3 which then leads to a fifth flexible tube 85 terminating in correspondence of said end 72 where a connector can be present.

Of course depending upon the treatment the blood circuit could also be provided with one or more infusion lines which can be branched to anyone of tubes 79 and/or 80 and/or 81 and/or 85.

In use tubular extensions 86 engaging the tube 82 together with one or more projections 87 are used to lock in operating position the air separator to a treatment machine panel. Looped tube 82 fits around the rollers of a peristaltic pump (not shown) carried on the front of the machine and liquid (blood or other liquid) can be pumped into the blood circuit. Of course depending upon the liquid to be pumped and upon the procedure to be put in place, proper connections with the patient and with the treatment unit have to be put in place as already well known in the art.

The described tubing can be made in any plastic material suitable for medical use, such as Single layer tubing made from Plasticized PVC (DEHP, or DEHP-free alternatives as plasticizer); multi-layer tubing including an outer layer of Plasticized PVC (DEHP, or DEHP-free alternatives as plasticizer), or Chlorine-free polymeric materials (e.g. thermoplastic elastomer polyurethanes, SEBS or SEPS-based compounds) and comprising an inner layer of polymeric material obtained from a combination of at least a polyolefin chosen in the group formed by polyethylene or polypropylene and at least one elastomer chosen in the group formed by SEPS or SEBS.

Figure 12:
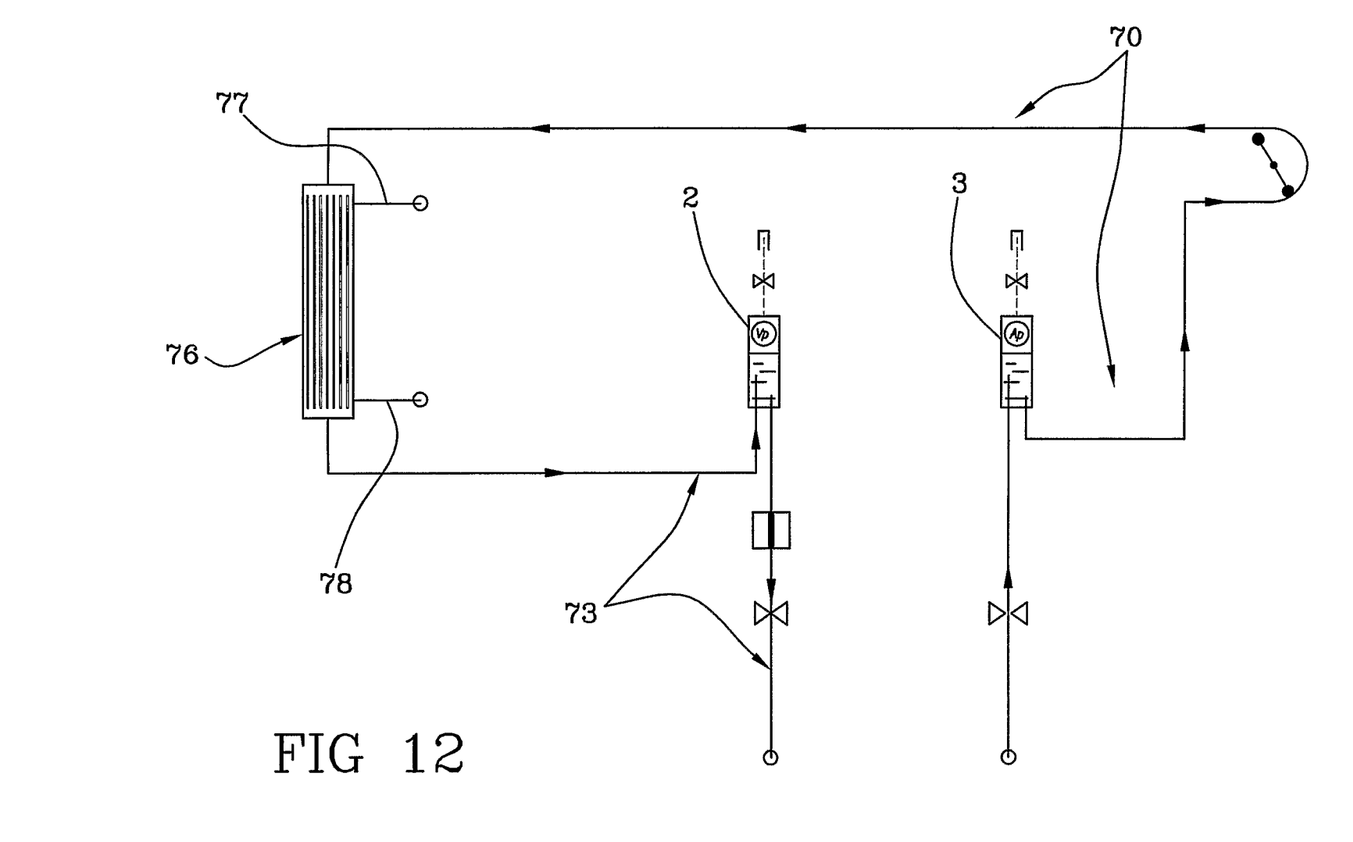
FIG. 12 is a schematic of an extracorporeal blood circuit adopting the air separator of the present invention.

FIG. 12 schematically shows the fluids flow circuit defined by the blood circuit and the air separator of FIG. 11 when they are connected to a blood treatment unit 76 of a blood treatment machine. The blood treatment unit can be for instance formed by a casing housing a semipermeable membrane separating a blood chamber and a treatment fluid chamber. The blood chamber of unit 76 is connected with the arterial and venous line ends 72 and 75.

The treatment fluid chamber is connected in use with an outlet line 77, for the spent treatment liquid, and with an inlet line 78, for the fresh treatment liquid (prepared by the blood treatment machine or coming from appropriate containers. Of course in case of treatments where no fresh liquid is required, then the treatment fluid chamber is only connected with outlet line 77.

Depending upon the blood treatment to be performed the blood circuit can be connected to corresponding connectors leading to a blood chamber of a dialyzer, of a hemofilter, of a plasmafilter, of an ultrafilter, of an hemodiafilter or of other treatment unit.

Figure 7B:
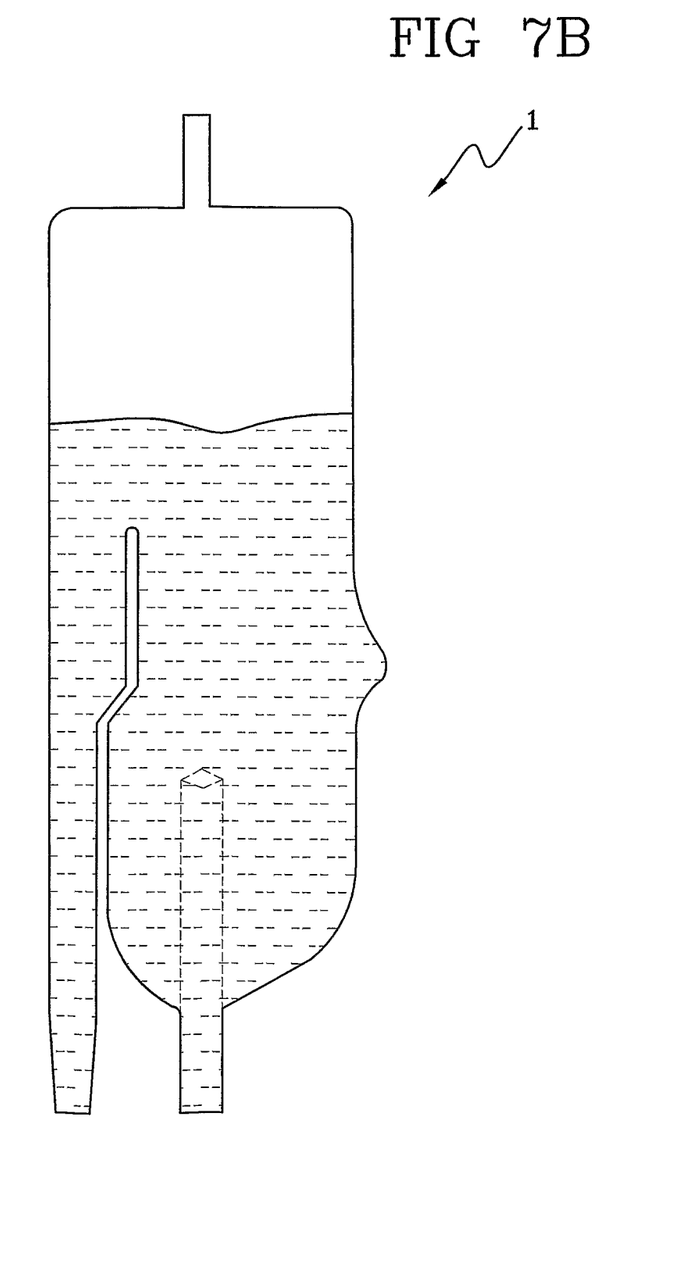
Figure 8B:
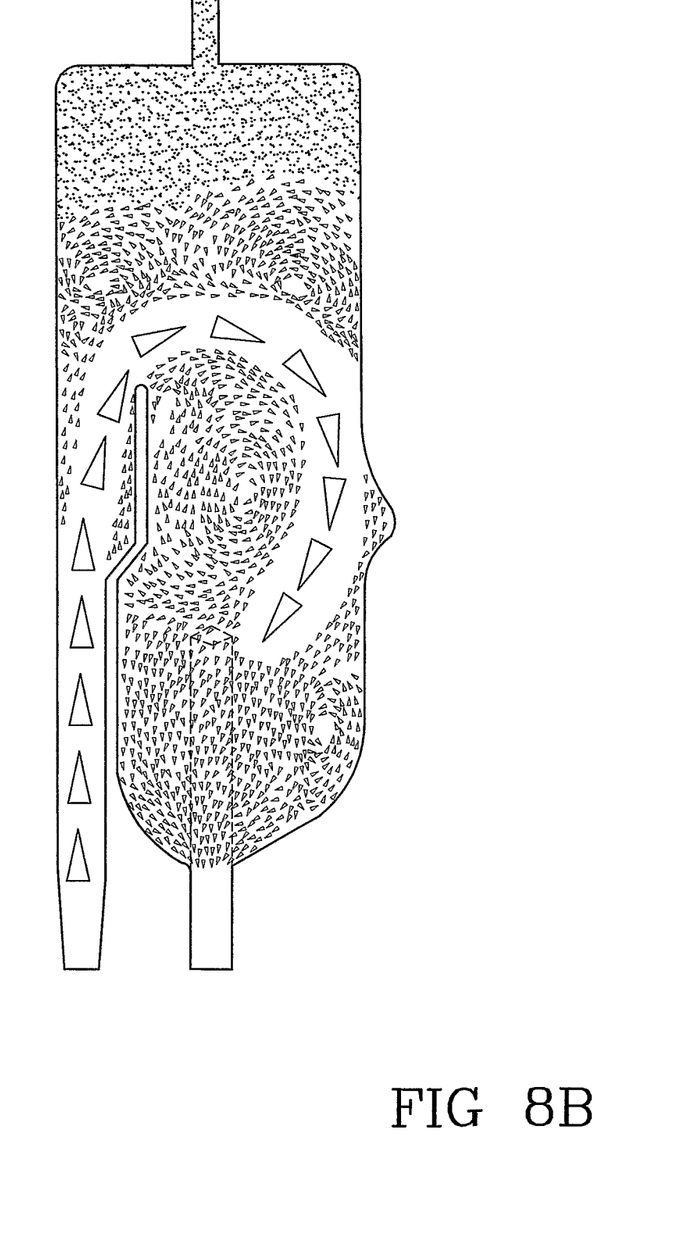

During treatment or during other procedures (such as priming or rinsing) liquid is pumped into the first blood chamber via the tube 79, the channel 14 directs the liquid towards the air separator top wall and provides for a uniform speed reduction in the flow as the channel is relatively long as compared to the chamber vertical and relatively wide in correspondence of the orifice. Therefore the liquid leaves the channel in a position which is sufficiently distant from the outlet port; moreover the direction of the flow, the speed reduction and uniform flow allow for a very efficient de-bubbling with no foam creation and minimal perturbations in correspondence of the air-blood interface (see FIG. 7B). Significant is the comparison of FIGS. 7A and 7B wherein one can easily see how the air separator of the invention provides for significant reduction in the perturbation and for a more stable liquid level. Moreover the distance of the orifice 15 from the outlet port 11, the geometry of the first channel and of the first chamber, and the specific position of the filter give as a result that the filter surface does not present areas of stagnation, thereby reducing the risk of clotting or of trapping bubbles. FIGS. 8A and 8B emphasize the improvement offered by the present invention as the entire filter 19 surface is touched by fluid having a certain sufficiently high speed. By contrast the filter of the prior art chamber of FIG. 8A presents a top region of fluid stagnation.

The invention claimed is:

1. Air separator for extracorporeal fluid treatment sets comprising:
 a first chamber where fluid can be received, the first chamber presenting:
  a bottom wall,
  a top wall,
  a lateral wall extending between the top and bottom walls,
 an inlet port and an outlet port associated to the bottom wall and in fluid communication with the first chamber,
 a first channel extending along at least a portion of the lateral wall and having a first end, directly connected to the inlet port, and a second end terminating in an orifice which is closer to said top wall than to said bottom wall, wherein said first channel has a first portion extending from the first end and at least a second portion terminating at the second end, the second end terminating where the fluid may first flow laterally out of the first channel and into the first chamber, the second portion presenting a flow passage cross section greater than that of the first portion, wherein the configuration of the first channel provides for a speed reduction of flow therethrough.

2. Air separator according to claim 1, wherein at least the second portion has a continuously and progressively increasing flow passage cross section.

3. Air separator according to claim 1, wherein the flow passage cross section of the first portion and the flow passage cross section of the second portion are substantially constant.

4. Air separator according to claim 3, wherein said first channel comprises a connection portion extending between the second portion and the first portion.

5. Air separator according to claim 4, wherein the connection portion has a progressively increasing flow passage cross section.

6. Air separator according to claim 4, wherein the connection portion comprises at least one aperture that puts into communication the first channel directly with the first chamber.

7. Air separator according to claim 1, wherein the first portion and the second portion extend in correspondence of and substantially parallel to the lateral wall of the first chamber.

8. Air separator according to claim 1, wherein the first portion is longer than the second portion.

9. Air separator according to claim 1, wherein the orifice opens into the first chamber and faces said top wall.

10. Air separator according to claim 9, wherein said orifice extends on a plane perpendicular to the lateral wall of the first chamber.

11. Air separator according to claim 1, wherein a ratio A1/A3 is comprised between 1.5 and 2.5, where:
   A1 represents the measure of the flow passage cross section area of the first channel in correspondence of said orifice,
   A3 represents the measure of the flow passage cross section area of the first channel in correspondence of the first portion.

12. Air separator according to claim 1 wherein a ratio D2/D1 is greater than 0.5, where:
   D1 represents the measure of the distance between top wall inner surface of the first chamber and bottom wall inner surface of the first chamber,
   D2 represents the measure of the distance between the horizontal plane where the orifice of the first channel extends and the bottom wall inner surface of the first chamber.

13. Air separator according to claim 1, wherein ratio A1/A2 is greater than 0.25 and less than 0.75, where:
   A1 represents the measure of the flow passage cross section area of the first channel in correspondence of said orifice,
   A2 represents the measure of the flow passage cross section area of the first chamber in correspondence of a section horizontally aligned with the orifice.

14. Air separator according to claim 1, comprising a filter engaged to the bottom wall in correspondence of the outlet port.

15. Air separator according to claim 14, wherein the filter axially extends into the first chamber according to a direction substantially parallel to the first channel, this latter being parallel to lateral wall.

16. Air separator according to claim 15, wherein the filter presents an overall axial extension substantially not greater than 70% of the measure of the distance between the horizontal plane where the orifice of the first channel extends and the bottom wall inner surface of the first chamber.

17. Air separator according to claim 16, wherein the filter has an axial extension not greater than that of the first portion of said first channel.

18. Air separator according to claim 1, wherein the first channel and the first chamber are made in one single plastic piece.

19. Air separator according to claim 1, wherein the air separator has a flattened structure, said first channel and said first chamber having a substantially square shaped transverse section.

20. Air separator according to claim 1, wherein said lateral wall presents:
   a front wall,
   a rear wall spaced from the front wall, and
   side walls extending between said front and rear walls,
   said air separator comprising an intermediate wall extending between the front and rear walls and laterally delimiting said channel in cooperation with one of said side walls.

21. Air separator according to claim 20, wherein said intermediate wall presents a first wall portion parallel to said one side wall, a second wall portion parallel to the same side wall and a deflecting portion connecting said first and second portion thereby forming said first portion, said connection portion and said second portion.

22. Air separator according to claim 1 comprising:
   a second chamber positioned in side by side relationship with respect to said first chamber,
   said second chamber being delimited by respective bottom wall, top wall, and lateral wall extending between the top and bottom walls, and being provided with respective inlet and outlet ports.

23. Air separator according to claim 22, wherein said lateral wall of the second chamber presents:
   a front wall,
   a rear wall spaced from the front wall, and
   side walls extending between said front and rear walls, said first and second chamber being in one single piece and sharing a common side wall which extends in correspondence of a central zone of the air separator.

24. Air separator according to claim 23, comprising a second channel extending parallel to the lateral wall of the second chamber and having a first end, connected to the inlet port, and a second end terminating into the second chamber, the second channel having constant cross section and presenting a deflector in correspondence of its second end defining an orifice facing the lateral wall of the second chamber.

25. Air separator according to claim 24, wherein the orifice of the second channel is substantially at the same height as the orifice of the first channel.

26. Air separator according to claim 1, wherein the lateral wall of said first chamber comprises pressure transducer means and wherein said first channel ends immediately below said pressure transducer means.

27. Air separator according to claim 22, further comprising a second channel extending parallel to the lateral wall of the second chamber and having a first end, connected to the inlet port, and a second end terminating into the second chamber, wherein the lateral wall of said second chamber comprises pressure transducer means and wherein said second channel ends immediately below said pressure transducer means.

28. Air separator for extracorporeal fluid treatment sets comprising:
   a first chamber where fluid can be received, the first chamber presenting:
      a bottom wall,
      a top wall,
      a lateral wall extending between the top and bottom walls,
   an inlet and an outlet port associated to the bottom wall and in fluid communication with the first chamber,
   a first channel having a first portion connected to the inlet port, and a second portion terminating where the fluid may first flow laterally out of the first channel and into the first chamber, wherein each of the flow passage cross section of the first portion and the flow passage cross section of the second portion are substantially constant and the second portion flow passage cross section is greater than that of the first portion, wherein the configuration of the first channel provides for a speed reduction of flow therethrough.

29. Air separator according to claim 28, wherein ratio A1/A2 is greater than 0.25 and less than 0.75, where:
- A1 represents the measure of the flow passage cross section area of the first channel in correspondence of said orifice,
- A2 represents the measure of the flow passage cross section area of the first chamber in correspondence of a section horizontally aligned with the orifice.

30. Air separator according to claim 28, wherein a ratio D2/D1 is greater than 0.5, where:
- D1 represents the measure of the distance between top wall inner surface of the first chamber and bottom wall inner surface of the first chamber,
- D2 represents the measure of the distance between the horizontal plane where the orifice of the first channel extends and the bottom wall inner surface of the first chamber.

31. Air separator according to claim 28, wherein ratio A1/A2 is greater than 0.25 and less than 0.75, where:
- A1 represents the measure of the flow passage cross section area of the first channel in correspondence of said orifice,
- A2 represents the measure of the flow passage cross section area of the first chamber in correspondence of a section aligned with the orifice.

32. Air separator for extracorporeal fluid treatment sets comprising:
- a first chamber where fluid can be received, the first chamber presenting:
  - a bottom wall,
  - a top wall,
  - a lateral wall extending between the top and bottom walls,
- an inlet port and an outlet port associated to the bottom wall and in fluid communication with the first chamber,
- a first channel extending along at least a portion of the lateral wall and having a first end, directly connected to the inlet port, and a second end terminating in an orifice which is closer to said top wall than to said bottom wall, wherein said first channel has a first portion extending from the first end and at least a second portion terminating at the second end, the second end terminating where the fluid may first flow laterally out of the first channel and into the first chamber, the second portion presenting a flow passage cross section greater than that of the first portion, wherein the configuration of the first channel provides for a speed reduction of flow therethrough, said air separator comprising at least one item selected from the group consisting of:
- a venous line which has at least one end designed to be connected to a patient and another end designed to be connected with a blood treatment unit, said venous line including a first flexible tube engaged to the inlet port of the first chamber, a second flexible tube engaged to the outlet port of the first chamber,
- an arterial line which has at least one end designed to be connected to a patient and another end designed to be connected with a blood treatment unit, said arterial line including a third flexible tube engaged to an inlet port of a second chamber, and a fourth flexible tube engaged to an outlet port of the second chamber and to one wall of said second chamber for forming a loop which is symmetric about a loop axis transverse to the lateral wall of the second chamber.

33. Blood treatment machine comprising:
- a dialysis liquid preparation module for preparing dialysis liquid,
- at least a waste line for receiving spent dialysate,
- a blood treatment unit having a first treatment chamber connected to the dialysis liquid preparation module and to the waste line, and a second treatment chamber separated from the first treatment chamber by means of a semipermeable membrane, and
- an air separator for extracorporeal fluid treatment sets comprising:
- a first chamber where fluid can be received, the first chamber presenting:
  - a bottom wall,
  - a top wall,
  - a lateral wall extending between the top and bottom walls,
- an inlet port and an outlet port associated to the bottom wall and in fluid communication with the first chamber,
- a first channel extending along at least a portion of the lateral wall and having a first end, directly connected to the inlet port, and a second end terminating in an orifice which is closer to said top wall than to said bottom wall, wherein said first channel has a first portion extending from the first end and at least a second portion terminating at the second end, the second end terminating where the fluid may first flow laterally out of the first channel and into the first chamber, the second portion presenting a flow passage cross section greater than that of the first portion, wherein the configuration of the first channel provides for a speed reduction of flow therethrough, said air separator comprising at least one item selected from the group consisting of:
- a venous line which has at least one end designed to be connected to a patient and another end designed to be connected with a blood treatment unit, said venous line including a first flexible tube engaged to the inlet port of the first chamber, a second flexible tube engaged to the outlet port of the first chamber,
- an arterial line which has at least one end designed to be connected to a patient and another end designed to be connected with a blood treatment unit, said arterial line including a third flexible tube engaged to an inlet port of a second chamber, and a fourth flexible tube engaged to an outlet port of the second chamber and to one wall of said second chamber for forming a loop which is symmetric about a loop axis transverse to the lateral wall of the second chamber, wherein the arterial line is connected to an inlet of the second chamber and the venous line is connected to an outlet of the second chamber.

* * * * *